(12) United States Patent
De Nanteuil et al.

(10) Patent No.: US 8,247,441 B2
(45) Date of Patent: Aug. 21, 2012

(54) CHROMENE COMPOUNDS, A PROCESS FOR THEIR PREPARATION AND PHARMACEUTICAL COMPOSITIONS CONTAINING THEM

(75) Inventors: Guillaume De Nanteuil, Suresnes (FR); Bernard Cimetiere, Paris (FR); Anne Dekeyne, Cernay la Ville (FR); Mark Millan, Le Pecq (FR)

(73) Assignee: Les Laboratoires Servier, Suresnes Cedex (FR)

( * ) Notice: Subject to any disclaimer, the term of this patent is extended or adjusted under 35 U.S.C. 154(b) by 10 days.

(21) Appl. No.: 12/804,355

(22) Filed: Jul. 20, 2010

(65) Prior Publication Data

US 2011/0021490 A1 Jan. 27, 2011

(30) Foreign Application Priority Data

Jul. 21, 2009 (FR) ...................... 09 03572

(51) Int. Cl.
*A61K 31/407* (2006.01)
*C07D 209/58* (2006.01)
(52) U.S. Cl. ....................... 514/411; 548/427
(58) Field of Classification Search .................. 548/427
See application file for complete search history.

(56) References Cited

FOREIGN PATENT DOCUMENTS
EP 0887350 12/1998

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/O9/24/alzheimers.drug.ap/indexhtml>.*
Dementia [online], retrieved on Sep. 28, 2011. Retrieved from the internet, URL; http://en.wikipedia.org/wiki/Dementia.*
A. Yarkov, et al., "Behavioral effects of dopamine agonists and antagonists in MPTP-lesioned D3 receptor knockout mice" Pharmacology, Biochemistry and Behavior, vol. 76, No. 3-4, p. 551-562, 2003.
F. Novi, et al., "Partial agonist actions of aripipraxolea dn the candidate antipsychotics S33592, bifeprunox N-desmethylcyclozapine and preclamol at . . . " Journal Fo Neurochemistry, vol. 102, No. 4, p. 1410-1424, 2007.
M. Millan, et al., "S33084, a novel potent selective, and competitive antagonist at dopamine D3-receptors: II Functional and behavioral profile compared with GR218,231 and L741,626" Journal of Pharmacology and Experimental Therapeutics, vol. 293, No. 3, p. 1063-1073, 2000.
M. Millan, et al., "S33138 (N-[4-[2-[((3aS,9bR)-8-cyano-2=1,3a, 4, 9b-tetrahydro{1}benzopyrano[3,4-c]pyrrol-2(3H)-yl)ethyl]phenylacetamide]]), a preferential dopamine D3 versus . . . " Journal of Pharmacology and Experimental Therapeutics, vol. 324, No. 3, p. 1212-1226 2008.
Preliminary Search Report for FR0903572 of Apr. 30, 2010.
T. Dubuffet, et al., "Novel benzopyrano [3,4-c]pyrrole derivatives as petent and selective dopamine D3 receptor antagonists" Bioorganic and Medicinal Chemistry Letters, vol. 9, No. 14, p. 2059-2064, 1999.
Richtand, et al., Neurosci. Behav. Rev., 2001, 25, 427-443.

* cited by examiner

*Primary Examiner* — Shawquia Young
(74) *Attorney, Agent, or Firm* — Hueschen and Sage

(57) ABSTRACT

The invention relates to compounds of formula (I):

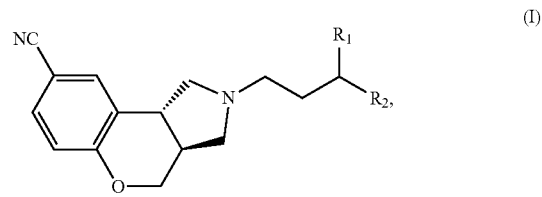

wherein $R_1$ and $R_2$ together form the following carbon-containing chain:

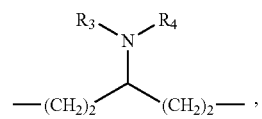

wherein:
  $R_3$ represents a hydrogen atom or an alkyl group,
  $R_4$ represents a hydrogen atom or an alkyl, aryl, heteroaryl, 3,4-dioxocyclobutenyl, alkylcarbonyl, cycloalkylcarbonyl, heterocycloalkylcarbonyl, benzoyl, arylsulphonyl or heteroarylsulphonyl group, each of those groups optionally being substituted,
  or $R_3$ and $R_4$ together with the nitrogen atom carrying them form a 5- to 8-membered ring, the ring thereby formed optionally being substituted.
Medicinal products containing the same which are useful in treating conditions requiring a D3 receptor antagonist.

13 Claims, No Drawings

CHROMENE COMPOUNDS, A PROCESS FOR THEIR PREPARATION AND PHARMACEUTICAL COMPOSITIONS CONTAINING THEM

The present invention relates to new chromene compounds, to a process for their preparation and to pharmaceutical compositions containing them.

It is well established that the dopaminergic pathways projecting to the limbic structures and the frontal cortex play important parts in the control of mood, in reward phenomena, in motor function and in cognition. $D_3$ dopaminergic receptors are present in high concentrations in those cortical and limbic structures such as the nucleus accumbens, the globus pallidus, the thalamus and the frontal cortex, whilst their density is relatively low in the striatum. As a consequence, they are a target of choice for psychotropic medicaments (Psychopharmacology, 1998, 135, 1-16; CNS Neurol. Disord. Drug Targets, 2006, 5, 25-43).

Blocking $D_2$ receptors brings about an improvement in positive symptoms but is also associated with catalepsy, with a reduction in cognitive function and with effects which may induce depression (CNS Drug Discov., 2006, 1, 271-88; Drug Discov. Today, 2005, 10, 917-25). Blocking $D_3$ receptors, however, although its impact on positive symptoms has not been definitely demonstrated, has a favourable influence on mood, improves cognitive function and counters catalepsy (Therapie 2008, 63, 187-229).

These observations suggest that a compound having an optimised profile, by way of preferential antagonist activity with respect to $D_3$ receptors and adequate antagonist activity with respect to $D_2$ receptors, could be situated within an ideal "therapeutic window" for optimum control of all the symptoms of schizophrenia whilst freeing itself of extrapyramidal side effects (catalepsy) and other disadvantages associated with highly selective blocking of each of the dopaminergic receptors (Drug Discov. Today, 2005, 10, 917-25; Therapie 2008, 63, 187-229).

On the basis of those observations and various results documented in the literature it will be understood that preference for $D_3$ over $D_2$ receptors provides the compounds of the invention with major value in use as medicaments in the treatment of schizophrenia and other psychoses (Drug Discov. Today, 2005, 10, 917-25; Neurosci. Behav. Rev., 2001, 25, 427-43), and abuse of drugs, including "recidivism" (Brain Res. Rev., 2005, 49, 77-105; J. Med. Chem., 2005, 48, 3664-79): for example, with the psychostimulants cocaine and amphetamine (Int. J. Neuropsychopharmacol., 2007, 10, 167-81; J. Pharmacol. Exp. Ther., 2007, 321, 573-82), nicotine (Neuropsychopharmacol., 2003, 28, 1272-80; Int. J. Neuropsychopharmacol., 2006, 9, 585-602), opiates (Synapse, 2003, 48, 154-6; Psychopharmacology, 2004, 175, 127-33) and ethanol (Pharmacol. Biochem. Behav., 2005, 81, 190-7; FASEB J., 2007, 20, 2223-33). The products of the invention are also capable of being used in the treatment of disorders caused by stress such as anxious states and toxicomania (Psychopharmacology, 2004, 176, 57-65; Prog. Neurobiol., 2003, 70, 83-244), the treatment of unipolar and bipolar depressive states (Eur. Neuropsychopharmacol., 2008, 18, 271-7; Mol. Interv., 2008, 8, 230-41), the treatment of impulsive behaviours such as obsessive-compulsive disorders (Psychiatry Res., 2003, 119, 1-10; Am. J. Med. Genet. B Neuropsychiatr. Genet., 2006, 141B, 409-13), and aggressiveness (J. Neural. Transm., 2003, 110, 561-72), the treatment of Parkinson's disease, when administered on their own or in association with dopaminergic agonists or L-DOPA (Neurobiol. Dis., 2009, in press; Exp. Neurol., 2004, 188, 128-38), the treatment of essential tremor (PNAS, 2006, 103, 10753-8; Brain, 2007, 130, 1456-64), disorders of memory and other cognitive disorders associated with psychiatric and neurological diseases such as dementias and Alzheimer's disease (Psychopharmacology, 2005, 179, 567-75; J. Neurochem., 2007, 100, 1047-61), developmental disorders in children or adolescents such as autistic spectrum disorder and attention-deficit hyperactivity disorder (Biol. Psychiatry, 2008, 65, 625-30), the treatment of pain, for example in association with opiates (Psychopharmacology, 1999, 144, 239-47; Prog. Neurobiol., 2002, 66, 355-474), or also of nausea caused, for example, by cytotoxic agents and dopaminergic agonists (J. Neural Transm., 1999, 105, 1045-61; Eur. J. Pharmacol., 1996, 301, 143-9). The compounds of the invention are also useful in the treatment of premature ejaculation (J. Sex. Med. 2009, 6, 980-8; Br. J. Pharmacol. 2008, 154, 1150-9) and also in renal protection, for example associated with diabetes or with chronic treatment with a metabolism-disrupting antipsychotic agent (Lab. Investigation, 2006, 86, 262-74; Naunyn Schmiedebergs Arch. Pharmacol., 2005, 371, 420-7).

The compounds of this invention, besides being new, have especially valuable properties in that they bind powerfully and preferentially to $D_3$ dopaminergic receptors.

More specifically, the present invention relates to compounds of formula (I):

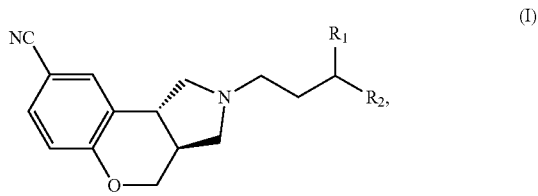

wherein $R_1$ and $R_2$ together form the following carbon-containing chain:

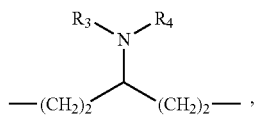

wherein:
$R_3$ represents a hydrogen atom or a linear or branched $(C_1-C_6)$alkyl group,
$R_4$ represents:
  a hydrogen atom,
  a linear or branched $(C_1-C_6)$alkyl, aryl, heteroaryl or 3,4-dioxocyclobutenyl group, each of those groups optionally being substituted by one or more identical or different groups selected from halogen; linear or branched $(C_1-C_6)$alkyl; linear or branched $(C_1-C_6)$alkylcarbonyl; carboxy; hydroxy; cyano; nitro; aminocarbonyl which is unsubstituted or substituted by one or more linear or branched $(C_1-C_6)$alkyl groups; and amino which is unsubstituted or substituted by one or two linear or branched $(C_1-C_6)$alkyl groups,
  a group —$COR_5$,
  a group —$SO_2R_5$,
$R_5$ represents a linear or branched $(C_1-C_6)$alkyl, $(C_3-C_8)$ cycloalkyl, heterocycloalkyl, aryl or heteroaryl group, each of those groups optionally being substituted by one or more identical or different groups selected from halogen; linear or branched $(C_1$-$C_6)$alkyl; linear or branched $(C_1$-$C_6)$alkylcarbonyl; carboxy; hydroxy; cyano; nitro; aminocarbonyl which is unsubstituted or substituted by one or more linear or branched $(C_1$-$C_6)$alkyl groups; and amino which is unsubstituted or substituted by one or two linear or branched $(C_1$-$C_6)$alkyl groups, or $R_3$ and $R_4$, together with the nitrogen atom carrying them, form a 5- to 8-membered ring, the ring thereby defined optionally being substituted by one or more identical or different groups selected from halogen; linear or branched $(C_1$-$C_6)$alkyl; hydroxy; oxo; and amino which is unsubstituted or substituted by one or two linear or branched $(C_1$-$C_6)$alkyl groups, to their positional isomers, to their enantiomers, to their diastereoisomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, acetic acid, trifluoroacetic acid, lactic acid, malonic acid, succinic acid, glutamic acid, fumaric acid, maleic acid, citric acid, oxalic acid, methanesulphonic acid, benzenesulphonic acid, camphoric acid etc.

Among the pharmaceutically acceptable bases there may be mentioned, without implying any limitation, sodium hydroxide, potassium hydroxide, triethylamine, tert-butylamine etc.

An aryl group is understood to be a phenyl or naphthyl group.

A heteroaryl group is understood to be a monocyclic or bicyclic group in which at least one ring is aromatic, containing from 5 to 11 ring members and from 1 to 4 hetero atoms selected from nitrogen, oxygen and sulphur.

The term heterocycloalkyl refers to a mono- or bi-cyclic, non-aromatic group containing from 4 to 11 ring members and having from 1 to 4 hetero atoms selected from nitrogen, oxygen and sulphur.

A preferred aryl group is a phenyl group.

Preferred heteroaryl groups are pyridyl and pyrimidinyl groups.

A preferred heterocycloalkyl group is an azetidine group.

In the compounds of formula (I), $R_3$ preferably represents a hydrogen atom or a methyl group.

The compounds of formula (I) are advantageously compounds wherein $R_4$ represents a hydrogen atom or a linear or branched $(C_1$-$C_6)$alkyl group.

Preferred compounds of the invention are those wherein $R_4$ represents the group —$COR_5$, where $R_5$ is as defined hereinbefore.

Other preferred compounds of the invention are those wherein $R_4$ represents the group —$SO_2R_5$, where $R_5$ is as defined hereinbefore.

The $R_5$ group preferably represents a linear or branched $(C_1$-$C_6)$alkyl group, a $(C_3$-$C_8)$cycloalkyl group, an aryl group or a heteroaryl group.

More especially, preferred compounds of formula (I) are compounds wherein $R_4$ represents —$COR_5$, where $R_5$ is a linear or branched $(C_1$-$C_6)$alkyl group.

Another preferred possibility for the compounds of formula (I) consists of $R_4$ representing —$COR_5$ where $R_5$ is an optionally substituted $(C_3$-$C_8)$cycloalkyl group.

The compounds of formula (I) preferably are compounds wherein $R_4$ represents —$COR_5$ where $R_5$ is an optionally substituted aryl group.

More especially, the compounds of formula (I) are compounds wherein $R_4$ represents —$SO_2R_5$ where $R_5$ is an optionally substituted aryl or heteroaryl group.

Another advantageous possibility consists of $R_3$ and $R_4$, together with the nitrogen atom carrying them, forming a 5-membered ring, the ring thereby formed optionally being substituted.

Preferred compounds of the invention are:
(3aS,9bR)-2-[2-(trans-4-aminocyclohexyl)ethyl]-1,2,3,3a,4, 9b-hexahydrochromeno[3,4-c]pyrrole-8-carbonitrile;
(3aS,9bR)-2-{2-[trans-4-(methylamino)cyclohexyl]ethyl}- 1,2,3,3a,4,9b-hexahydrochromeno[3,4-c]pyrrole-8-carbonitrile;
(3aS,9bR)-2-{2-[trans-4-(dimethylamino)cyclohexyl] ethyl}-1,2,3,3a,4,9b-hexahydrochromeno[3,4-c]pyrrole-8-carbonitrile;
N-(trans-4-{2-[(3aS,9bR)-8-cyano-1,3a,4,9b-tetrahydrochromeno[3,4-c]pyrrol-2(3H)-yl]ethyl}cyclohexyl)acetamide;
N-(trans-4-{2-[(3aS,9bR)-8-cyano-1,3a,4,9b-tetrahydrochromeno[3,4-c]pyrrol-2(3H)-yl]ethyl}cyclohexyl)-2,2-dimethylpropanamide;
N-(trans-4-{2-[(3aS,9bR)-8-cyano-1,3a,4,9b-tetrahydrochromeno[3,4-c]pyrrol-2(3H)-yl]ethyl}cyclohexyl)-N-methylacetamide;
N-(trans-4-{2-[(3aS,9bR)-8-cyano-1,3a,4,9b-tetrahydrochromeno[3,4-c]pyrrol-2(3H)-yl]ethyl}cyclohexyl)cyclobutanecarboxamide;
N-(trans-4-{2-[(3aS,9bR)-8-cyano-1,3a,4,9b-tetrahydrochromeno[3,4-c]pyrrol-2(3H)-yl]ethyl}cyclohexyl)cyclopropanecarboxamide;
N-(trans-4-{2-[(3aS,9bR)-8-cyano-1,3a,4,9b-tetrahydrochromeno[3,4-c]pyrrol-2(3H)-yl]ethyl}cyclohexyl)-3,3-difluorocyclobutanecarboxamide;
cis-N-(trans-4-{2-[(3aS,9bR)-8-cyano-1,3a,4,9b-tetrahydrochromeno[3,4-c]pyrrol-2(3H)-yl]ethyl}cyclohexyl)-3-hydroxycyclobutanecarboxamide;
N-(trans-4-{2-[(3aS,9bR)-8-cyano-1,3a,4,9b-tetrahydrochromeno[3,4-c]pyrrol-2(3H)-yl]ethyl}cyclohexyl)-N-methylcyclobutanecarboxamide;
N-(trans-4-{2-[(3aS,9bR)-8-cyano-1,3a,4,9b-tetrahydrochromeno[3,4-c]pyrrol-2(3H)-yl]ethyl}cyclohexyl)benzamide;
4-chloro-N-(trans-4-{2-[(3aS,9bR)-8-cyano-1,3a,4,9b-tetrahydrochromeno[3,4-c]pyrrol-2(3H)-yl] ethyl}cyclohexyl)benzamide;
N-(trans-4-{2-[(3aS,9bR)-8-cyano-1,3a,4,9b-tetrahydrochromeno[3,4-c]pyrrol-2(3H)-yl)ethyl]cyclohexyl)-4-fluorobenzenesulphonamide;
N-(trans-4-{2-[(3aS,9bR)-8-cyano-1,3a,4,9b-tetrahydrochromeno[3,4-c]pyrrol-2(3H)-yl)ethyl]cyclohexyl)-3-pyridinesulphonamide;
4-chloro-N-(trans-4-{2-[(3aS,9bR)-8-cyano-1,3a,4,9b-tetrahydrochromeno[3,4-c]pyrrol-2(3H)-yl] ethyl}cyclohexyl)benzenesulphonamide;
(3aS,9bR)-2-{2-[trans-4-(2-oxopyrrolidin-1-yl)cyclohexyl] ethyl}-1,2,3,3a,4,9b-hexahydrochromeno[3,4-c]pyrrole-8-carbonitrile.

The addition salts of preferred compounds of the invention with a pharmaceutically acceptable acid or base form an integral part of the invention.

The invention relates also to a process for the preparation of compounds of formula (I), characterised in that there is used as starting material a compound of formula (II):

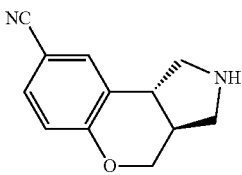

(II)

which is subjected to a reductive amination reaction in the presence of a reducing agent, such as sodium triacetoxyborohydride or sodium cyanoborohydride, and a compound of formula (III):

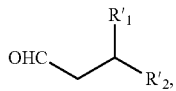

(III)

wherein R'$_1$ and R'$_2$ together form the following carbon-containing chain:

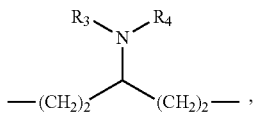

wherein R$_3$ is as defined hereinbefore and R represents a protecting group for the amine function such as, for example, a tert-butyloxycarbonyl group, to yield the compound of formula (IV):

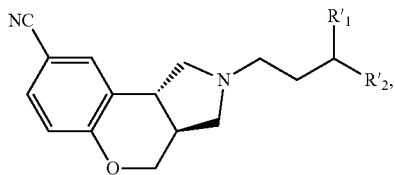

(IV)

wherein R'$_1$ and R'$_2$ are as defined hereinbefore, which is then subjected to a reaction deprotecting the amine function, for example in the presence of trifluoroacetic acid, to yield the compound of formula (I/a), a particular case of the compounds of formula (I):

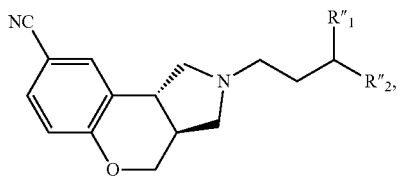

(I/a)

wherein R"$_1$ and R"$_2$ together form the following carbon-containing chain:

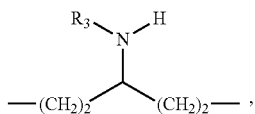

wherein R$_3$ is as defined hereinbefore, which compound of formula (I/a) is then, if necessary, subjected:

either to a reductive amination reaction with a reducing agent, such as sodium triacetoxyborohydride or sodium cyanoborohydride, in the presence of a compound of formula (V):

R'—CHO  (V), wherein R' represents a hydrogen atom or a linear or branched (C$_1$-C$_5$)alkyl group;

or to the action of a compound of formula (VI):

R"—Y  (VI), wherein Y represents a halogen atom or a hydroxy or linear or branched (C$_1$-C$_6$)alkoxy group, and R" represents an aryl, heteroaryl, 3,4-dioxocyclobutenyl, —COR$_5$ or —SO$_2$R$_5$ group, where R$_5$ is as defined hereinbefore, to yield the compound of formula (I/b), a particular case of the compounds of formula (I):

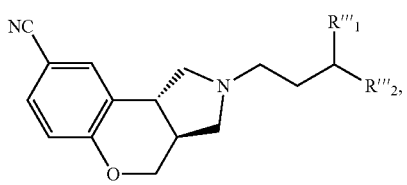

(I/b)

wherein R'''$_1$ and R'''$_2$ together form the following carbon-containing chain:

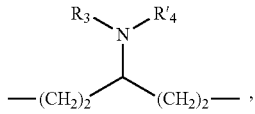

wherein R$_3$ is as defined hereinbefore and R'$_4$ represents a linear or branched (C$_1$-C$_6$)alkyl, aryl, heteroaryl, 3,4-dioxocyclobutenyl, —COR$_5$ or —SO$_2$R$_5$ group, where R$_5$ is as defined hereinbefore, a variant in the preparation of the compound of formula (I/b) consisting of using customary chemical reactions, once the step of coupling with the compound of formula (I/a) has been carried out, in order to subsequently modify the substituents of the compound of formula (VI), it then being possible for the compounds of formulae (I/a) and (I/b), which constitute the entirety of the compounds of formula (I), to be purified according to a customary separation technique, converted, if desired, into their addition salts with a pharmaceutically acceptable acid or base and separated, where appropriate, into their isomers, if they exist, according to a customary separation technique.

The compounds of formulae (II), (III), (V) and (VI) are commercially available or readily accessible to the person skilled in the art by means of customary chemical reactions or chemical reactions described in the literature.

The invention relates also to pharmaceutical compositions comprising as active ingredient at least one compound of formula (I) on its own or in combination with one or more inert, non-toxic excipients or carriers. Among the pharmaceutical compositions according to the invention there may be mentioned more especially those that are suitable for oral, parenteral (intravenous or subcutaneous) or nasal administration, tablets or dragées, sublingual tablets, capsules, lozenges, suppositories, creams, ointments, dermal gels, injectable preparations and drinkable suspensions.

The useful dosage varies according to the age and weight of the patient, the nature and severity of the disorder and the administration route, which may be nasal, rectal, parenteral or oral. Generally, the unit dose ranges from 1 to 500 mg per 24 hours for treatment in 1 to 3 administrations.

The Examples that follow illustrate the invention and do not limit it in any way. The structures of the described compounds were confirmed by customary spectroscopic techniques.

The Preparations described hereinbelow yield starting materials that are used in the synthesis of the compounds of the invention.

Preparation 1: Methyl trans-{4-[(tert-butoxycarbonyl)amino]cyclohexyl}acetate

To a mixture of 3.03 g of ethyl trans-(4-amino-cyclohexyl) acetate (17.7 mmol), obtained in 7 steps starting from bicyclo [2.2.2]oct-5-ene-2-carbonitrile, and 4.25 g of di-tert-butyl dicarbonate (19.54 mmol) in 60 ml of dichloromethane there are added 6.2 ml of triethylamine. The mixture is stirred for 2 hours at ambient temperature. 50 ml of saturated sodium bicarbonate solution are added. The solution is extracted with 3×20 ml of dichloromethane, washed with brine, dried ($MgSO_4$) and evaporated to yield the title product in the form of a white powder.

Melting point: 78° C.

Preparation 2: trans-{4-[(tert-Butoxycarbonyl)amino]cyclohexyl}acetaldehyde

To a solution of 1.78 g of the compound of Preparation 1 (6.6 mmol) in 35 ml of toluene, there are added dropwise, at −78° C., 11 ml of 1N DIBAL-H solution in hexane. The mixture is stirred for 10 minutes at −78° C. and is then treated with 1.08 ml of methanol in 2 ml of toluene (dropwise). It is allowed to come back up to ambient temperature and there are rapidly added, dropwise, 47 ml of a saturated aqueous solution of potassium sodium double tartrate (Seignette's salt). After stirring for 1 hour, the solution is extracted with ether, washed with water, dried ($MgSO_4$) and evaporated to yield the title product in the form of a white solid.

Melting point: 61-63° C.

Preparation 3: Methyl trans-{4-[(tert-butoxycarbonyl)(methyl)amino]cyclohexyl}acetate To a solution of 4.28 g of the compound of Preparation 1 (15.8 mmol) in 45 ml of DMF there are added 1.38 ml of methyl iodide and then 884 mg of sodium hydride. After stirring for 18 hours, the mixture is diluted with ether and water and then 0.1N HCl solution is added until the pH=3. The solution is extracted with ether, washed with water, dried ($MgSO_4$) and then evaporated. Purification by chromatography on a silica column using a mixture of cyclohexane/ethyl acetate (90/10) as eluant yields the title product in the form of a colourless oil.

Preparation 4: trans-{4-[(tert-Butoxycarbonyl)(methyl)amino]cyclohexyl}acetaldehyde The title product is obtained according to the procedure described in Preparation 2 using the product described in Preparation 3 as starting material.

Preparation 5: tert-Butyl (trans-4-{2-[(3aS,9bR)-8-cyano-1,3a,4,9b-tetrahydrochromeno[3,4-c]pyrrol-2(3H)-yl]ethyl}cyclohexyl)carbamate To 30 ml of dichloromethane there are successively added 1.08 g of (3aS,9bR)-1,2,3,3a,4,9b-hexahydrochromeno[3,4-c]pyrrole-8-carbonitrile (synthesised in accordance with *Bioorg. Med. Chem. Len.* 1999, 9, 2059-2064) (5.42 mmol), 1.58 g of the compound of Preparation 2 (6.5 mmol) and 1.61 g of sodium triacetoxyborohydride (7.59 mmol). The reaction mixture is stirred overnight at ambient temperature. The solution is then washed with 1N sodium hydroxide solution and then with brine, dried ($MgSO_4$) and evaporated. Purification on a silica column using a mixture of dichloromethane/methanol/ammonium hydroxide (99/1/0.1) as eluant yields the title product in the form of a white powder.

Preparation 6: tert-Butyl (trans-4-{2-[(3aS,9bR)-8-cyano-1,3a,4,9b-tetrahydrochromeno[3,4-c]pyrrol-2(3H)-yl]ethyl}cyclohexyl)methylcarbamate The title product is obtained according to the procedure described in Preparation 5, using as starting material the compound described in Preparation 4 instead of the product described in Preparation 2.

Preparation 7: Phthalic acid monomethyl ester

Dimethyl phthalate (15.73 mmol) is stirred for 24 hours at ambient temperature in 60 ml of ethanol with 15.73 ml of 1N sodium hydroxide solution. The solvent is evaporated off under reduced pressure at 40° C. and the reaction mixture is then diluted with water before bringing the pH to 3. The mixture is extracted with ethyl acetate, dried ($MgSO_4$) and evaporated to yield the title product in the form of an oil.

EXAMPLE 1

(3aS,9bR)-2-[2-(trans-4-Aminocyclohexyl)ethyl]-1,2,3,3a,4,9b-hexahydrochromeno[3,4-c]pyrrole-8-carbonitrile dihydrochloride To a solution of 1.5 g of the compound of Preparation 5 (3.5 mmol) in 30 ml of dichloromethane there are added 2.9 ml of trifluoroacetic acid. The mixture is stirred for 4.5 hours at ambient temperature and the solvent is evaporated off. The residue is partitioned between aqueous sodium carbonate solution and dichloromethane. The solution is extracted with dichloromethane, washed with water, dried ($K_2CO_3$) and evaporated to yield, after converting to a salt using 2 equivalents of 1N ethereal HCl, the title product in the form of a white powder.

Elemental Microanalysis:

|  | C | H | N | Cl |
|---|---|---|---|---|
| theoretical % | 60.30 | 7.34 | 10.55 | 17.80 |
| experimental % | 60.16 | 7.04 | 10.65 | 17.62 |

EXAMPLE 2

N-(trans-4-{2-[(3aS,9bR)-8-cyano-1,3a,4,9b-tetrahydrochromeno[3,4-c]pyrrol-2(3H)-yl]ethyl}cyclohexyl)acetamide hydrochloride To a solution of 699 mg (2.1 mmol) of the compound of Example 1 in 15 ml of dichloromethane there are added, at ambient temperature, 354 µl of triethylamine (1.2 eq.) and then 164 µl of acetyl chloride (1.1 eq.). After stirring for 2 hours at ambient temperature, the mixture is washed with water and dried (MgSO$_4$). Evaporating off the solvent followed by purifying on a silica column using a mixture of dichloromethane/methanol/ammonium hydroxide (97/3/0.3) as eluant yields, after converting to a salt in ethanol in the warm state using 1N ethereal HCl, the title product in the form of a white powder.

Melting point: 293° C.

Elemental Microanalysis:

|  | C | H | N | Cl |
|---|---|---|---|---|
| theoretical % | 65.41 | 7.49 | 10.40 | 8.78 |
| experimental % | 65.00 | 7.30 | 10.46 | 8.83 |

EXAMPLE 3

N-(trans-4-{2-[(3aS,9bR)-8-cyano-1,3a,4,9b-tetrahydrochromeno[3,4-c]pyrrol-2(3H)-yl]ethyl}cyclohexyl)cyclobutanecarboxamide hydrochloride The title product is obtained according to the procedure described in Example 2 using cyclobutanecarbonyl chloride instead of acetyl chloride.

Melting point: 291° C.

Elemental Microanalysis:

|  | C | H | N | Cl |
|---|---|---|---|---|
| theoretical % | 67.63 | 7.72 | 9.46 | 7.98 |
| experimental % | 66.95 | 7.72 | 9.20 | 7.90 |

EXAMPLE 4

N-(trans-4-{2-[(3aS,9bR)-8-cyano-1,3a,4,9b-tetrahydrochromeno[3,4-c]pyrrol-2(3H)-yl]ethyl}cyclohexyl)cyclopropanecarboxamide hydrochloride The title product is obtained according to the procedure described in Example 2 using cyclopropanecarbonyl chloride instead of acetyl chloride.

Melting point: 284° C.

Elemental Microanalysis:

|  | C | H | N | Cl |
|---|---|---|---|---|
| theoretical % | 67.04 | 7.50 | 9.77 | 8.25 |
| experimental % | 66.32 | 7.38 | 9.49 | 8.24 |

EXAMPLE 5

N-(trans-4-{2-[(3aS,9bR)-8-cyano-1,3a,4,9b-tetrahydrochromeno[3,4-c]pyrrol-2(3H)-yl]ethyl}cyclohexyl)benzamide hydrochloride The title product is obtained according to the protocol described in Example 2 using benzoyl chloride instead of acetyl chloride.

Melting point: 284° C.

Elemental Microanalysis:

|  | C | H | N | Cl |
|---|---|---|---|---|
| theoretical % | 69.59 | 6.92 | 9.02 | 7.61 |
| experimental % | 69.53 | 6.91 | 9.09 | 7.47 |

EXAMPLE 6

4-Chloro-N-(trans-4-{2-[(3aS,9bR)-8-cyano-1,3a,4,9b-tetrahydrochromeno[3,4-c]pyrrol-2(3H)-yl]ethyl}cyclohexyl)benzamide hydrochloride The title product is obtained according to the protocol described in Example 2 using 4-chlorobenzoyl chloride instead of acetyl chloride.

Melting point: 288° C.

Elemental Microanalysis:

|  | C | H | N | Cl |
|---|---|---|---|---|
| theoretical % | 64.80 | 6.24 | 8.40 | 14.17 |
| experimental % | 64.66 | 5.96 | 8.41 | 13.96 |

EXAMPLE 7

N-(trans-4-{2-[(3aS,9bR)-8-cyano-1,3a,4,9b-tetrahydrochromeno[3,4-c]pyrrol-2(3H)-yl]ethyl}cyclohexyl)-2,2-dimethylpropanamide hydrochloride The title product is obtained according to the protocol described in Example 2 using pivaloyl chloride instead of acetyl chloride.

Melting point: 314-317° C.

Elemental Microanalysis:

|  | C | H | N | Cl |
|---|---|---|---|---|
| theoretical % | 67.32 | 8.13 | 9.42 | 7.95 |
| experimental % | 67.04 | 8.13 | 9.25 | 7.82 |

EXAMPLE 8

N-(trans-4-{2-[(3aS,9bR)-8-cyano-1,3a,4,9b-tetrahydrochromeno[3,4-c]pyrrol-2(3H)-yl]ethyl}cyclohexyl)cyclopentanecarboxamide hydrochloride The title product is obtained according to the protocol described in Example 2 using cyclopentanecarbonyl chloride instead of acetyl chloride.

Melting point: 288° C.

Elemental Microanalysis:

|  | C | H | N | Cl |
|---|---|---|---|---|
| theoretical % | 68.18 | 7.92 | 9.17 | 7.74 |
| experimental % | 68.20 | 7.69 | 9.23 | 7.31 |

EXAMPLE 9

N-(trans-4-{2-[(3aS,9bR)-8-cyano-1,3a,4,9b-tetrahydrochromeno[3,4-c]pyrrol-2(3H)-yl]ethyl}cyclohexyl)-3-pyridinesulphonamide hydrochloride The title product is obtained according to the protocol described in Example 2 using pyridine-3-sulphonyl chloride (synthesised in accordance with J. Org. Chem. 1989, 54, 389-393) instead of acetyl chloride.

Melting point: 272° C.

Elemental Microanalysis:

|  | C | H | N | S | Cl |
|---|---|---|---|---|---|
| theoretical % | 59.69 | 6.21 | 11.14 | 6.37 | 7.05 |
| experimental % | 59.06 | 6.02 | 10.93 | 5.48 | 7.06 |

EXAMPLE 10

N-(trans-4-{2-[(3aS,9bR)-8-cyano-1,3a,4,9b-tetrahydrochromeno[3,4-c]pyrrol-2(3H)-yl]ethyl}cyclohexyl)-4-fluorobenzene sulphonamide hydrochloride The title product is obtained according to the protocol described in Example 2 using 4-fluorobenzenesulphonyl chloride instead of acetyl chloride.

Melting point: 300° C.

Elemental Microanalysis:

|  | C | H | N | S | Cl |
|---|---|---|---|---|---|
| theoretical % | 60.05 | 6.01 | 8.08 | 6.17 | 6.82 |
| experimental % | 59.28 | 5.90 | 7.90 | 5.68 | 6.49 |

EXAMPLE 11

4-Chloro-N-(trans-4-{2-[(3aS,9bR)-8-cyano-1,3a,4,9b-tetrahydrochromeno[3,4-c]pyrrol-2(3H)-yl]ethyl}cyclohexyl)benzenesulphonamide hydrochloride The title product is obtained according to the protocol described in Example 2 using 4-chlorobenzenesulphonyl chloride instead of acetyl chloride.

Melting point: 285° C.

Elemental Microanalysis:

|  | C | H | N | S | Cl |
|---|---|---|---|---|---|
| theoretical % | 58.21 | 5.82 | 7.83 | 5.98 | 13.22 |
| experimental % | 58.53 | 5.70 | 7.70 | 5.68 | 12.75 |

EXAMPLE 12

4-[(trans-4-{2-[(3aS,9bR)-8-Cyano-1,3a,4,9b-tetrahydrochromeno[3,4-c]pyrrol-2(3H)-yl]ethyl}cyclohexyl)carbamoyl]benzoic acid hydrochloride Step A: Methyl 4-[(trans-4-{2-[(3aS,9bR)-8-cyano-1,3a,4,9b-tetrahydrochromeno[3,4-c]pyrrol-2(31-1)-yl]ethyl}cyclohexyl)carbamoyl]benzoate The title product is obtained according to the protocol described in Example 2 using methyl 4-chlorocarbamoylbenzoate instead of acetyl chloride.

Step B: 4-[(trans-4-{2-[(3aS,9bR)-8-Cyano-1,3a,4,9b-tetrahydrochromeno[3,4-c]pyrrol-2(3H)-yl]ethyl}cyclohexyl)carbamoyl]benzoic acid hydrochloride 0.737 g of the product obtained in the Step above (1.68 mmol) is dissolved in 15 ml of ethanol and heated at reflux with 1.79 ml of 1N sodium hydroxide solution for 1.5 hours. The ethanol is then evaporated off, the reaction mixture is taken up in water, and then 3.6 ml of 1N hydrochloric acid are added at 0° C. The solid obtained is filtered off and dried in a desiccator.

Melting point: 298° C.

Elemental Microanalysis:

|  | C | H | N | Cl |
|---|---|---|---|---|
| theoretical % | 65.94 | 6.32 | 8.24 | 6.95 |
| experimental % | 66.22 | 5.83 | 8.19 | 6.28 |

EXAMPLE 13

2-[(trans-4-{2-[(3aS,9bR)-8-Cyano-1,3a,4,9b-tetrahydrochromeno[3,4-c]pyrrol-2(3H)-yl]ethyl}cyclohexyl)carbamoyl]benzoic acid hydrochloride

Step A: Methyl 4-[(trans-4-{2-[(3aS,9bR)-8-cyano-1,3a,4,9b-tetrahydrochromeno[3,4-c]pyrrol-2(3H)-yl]ethyl}cyclohexyl)carbamoyl]benzoate A solution of 1.21 g of the compound of Example 1 (in the form of the base) (3.72 mmol), 0.8 g of the compound of Preparation 7 (1.2 eq.), 0.78 g of 1-(3-dimethylaminopropyl)-3-ethyl-carbodiimide hydrochloride (1.1 eq.) and 50 mg of hydroxybenzotriazole in 80 ml of dichloromethane is stirred for 18 hours at ambient temperature. 37 ml of saturated aqueous sodium bicarbonate solution are added, and the mixture is then stirred for 15 minutes. After extraction with dichloromethane, drying (MgSO$_4$) and evaporation, the residue is purified by chromatography on a silica column using a mixture of dichloromethane/methanol/ammonium hydroxide (97/3/0.3) as eluant to yield the title product in the form of an oil.

Step B: 2-[(trans-4-{2-[(3aS,9bR)-8-Cyano-1,3a,4,9b-tetrahydrochromeno[3,4-c]pyrrol-2(3H)-yl]ethyl}cyclohexyl)carbamoyl]benzoic acid hydrochloride The title product is obtained according to the procedure described in Step B of Example 12, using the compound obtained in Step A above as starting material.

Melting point: 303° C.
Elemental Microanalysis:

|  | C | H | N | Cl |
|---|---|---|---|---|
| theoretical % | 65.94 | 6.32 | 8.24 | 6.95 |
| experimental % | 65.57 | 6.25 | 8.15 | 6.52 |

EXAMPLE 14

3-[(trans-4-{2-[(3aS,9bR)-8-Cyano-1,3a,4,9b-tetrahydrochromeno[3,4-c]pyrrol-2(3H)-yl]ethyl}cyclohexyl)carbamoyl]benzoic acid hydrochloride The title product is obtained according to the procedure described in Example 13 using commercially available monomethyl isophthalate instead of Preparation 7.

Melting point: 257° C.
Elemental Microanalysis:

|  | C | H | N | Cl |
|---|---|---|---|---|
| theoretical % | 65.94 | 6.32 | 8.24 | 6.95 |
| experimental % | 65.33 | 6.15 | 8.03 | 6.55 |

EXAMPLE 15

N-(trans-4-{2-[(3aS,9bR)-8-cyano-1,3a,4,9b-tetrahydrochromeno[3,4-c]pyrrol-2(3H)-yl]ethyl}cyclohexyl)azetidine-3-carboxamide dihydrochloride

Step A: tert-Butyl 3-[(trans-4-{2-[(3aS,9bR)-8-cyano-1,3a,4,9b-tetrahydrochromeno[3,4-c]pyrrol-2(3H)-yl]ethyl}cyclohexyl)carbamoyl]azetidine-1-carboxylate The title product is obtained according to the procedure described in Step A of Example 13 using 1-(tert-butoxycarbonyl)azetidine-3-carboxylic acid (synthesised in accordance with Biochemistry, 2001, 40, 5226-5232) instead of Preparation 7.

Step B: N-(trans-4-{2-[(3aS,9bR)-8-cyano-1,3a,4,9b-tetrahydrochromeno[3,4-c]pyrrol-2(3H)-yl]ethyl}cyclohexyl)azetidine-3-carboxamide dihydrochloride 2.82 g of the product obtained in the Step above (5.56 mmol) is stirred at ambient temperature in a mixture of 56 ml of dichloromethane and 5.6 ml of trifluoroacetic acid for 3 hours. The solvents are then evaporated off; concentrated sodium hydroxide solution is then added and the solution is then extracted with ethyl acetate, washed with 1N sodium hydroxide solution and brine, dried (MgSO$_4$) and evaporated. After converting to a salt in ethanol in the warm state using 1N ethereal HCl, the title product is obtained in the form of a powder.

Melting point: 283° C.
Elemental Microanalysis:

|  | C | H | N | Cl |
|---|---|---|---|---|
| theoretical % | 59.87 | 7.12 | 11.64 | 14.73 |
| experimental % | 59.67 | 6.84 | 11.42 | 14.56 |

EXAMPLE 16

1-Acetyl-N-(trans-4-{2-[(3aS,9bR)-8-cyano-1,3a,4,9b-tetrahydrochromeno[3,4-c]pyrrol-2(3H)-yl]ethyl}cyclohexyl)azetidine-3-carboxamide hydrochloride The title product is obtained according to the procedure described in Example 2 using as starting material the compound of Example 15 instead of the compound of Example 1.

Melting point: 251° C.
Elemental Microanalysis:

|  | C | H | N | Cl |
|---|---|---|---|---|
| theoretical % | 64.12 | 7.24 | 11.50 | 7.28 |
| experimental % | 63.88 | 7.16 | 11.29 | 7.27 |

EXAMPLE 17

N-(trans-4-{2-[(3aS,9bR)-8-cyano-1,3a,4,9b-tetrahydrochromeno[3,4-c]pyrrol-2(3H)-yl]
ethyl}cyclohexyl)-3,3-difluorocyclobutanecarboxamide hydrochloride The title product is obtained according to the procedure described in Step A of Example 13 using 3,3-difluorocyclobutanecarboxylic acid (synthesised in accordance with Synthetic Communications, 2005, 35, 657-662) instead of Preparation 7.
Melting point: 288° C.
Elemental Microanalysis:

|  | C | H | N | Cl |
|---|---|---|---|---|
| theoretical % | 62.56 | 6.72 | 8.75 | 7.39 |
| experimental % | 63.17 | 6.60 | 8.73 | 7.35 |

EXAMPLE 18 cis-N-(trans-4-{2-[0aS,9bR)-8-cyano-1,3a,4,913-tetrahydrochromeno[3,4-c]pyrrol-2(3H)-yl]
ethyl}cyclohexyl)-3-hydroxycyclobutanecarboxamide hydrochloride The title product is obtained according to the procedure described in Step A of Example 13 using 3-cis-hydroxycyclobutanecarboxylic acid (synthesised in accordance with patent specification US 2005/0020645) instead of Preparation 7.
Melting point: 269° C.
Elemental Microanalysis:

|  | C | H | N | Cl |
|---|---|---|---|---|
| theoretical % | 65.28 | 7.45 | 9.13 | 7.71 |
| experimental % | 65.28 | 7.26 | 9.07 | 7.65 |

EXAMPLE 19

(3aS,9bR)-2-{2-[trans-4-(2-oxopyrrolidin-1-yl)cyclohexyl]ethyl}-1,2,3,3a,4,9b-hexahydrochromeno[3,4-c]pyrrole-8-carbonitrile hydrochloride Step A: 4-Chloro-N-(trans-4-{2-[(3aS,9bR)-8-cyano-1,3a,4,9b-tetrahydrochromeno[3,4-c]pyrrol-2(3H)-yl]ethyl}cyclohexyl)butanamide The title product is obtained according to the procedure described in Example 2 using 4-chlorobutyryl chloride instead of acetyl chloride.

Step B: (3aS,9bR)-2-{2-[trans-4-(2-oxopyrrolidin-1-yl)cyclohexyl]ethyl}-1,2,3,3a,4,9b-hexahydrochromeno[3,4-c]pyrrole-8-carbonitrile hydrochloride 1.77 g of the product obtained in the Step above (4.12 mmol) is suspended in 3 ml of THF with 165 mg of sodium hydride, and is then heated at reflux for 18 hours. The cooled mixture is then poured into aqueous saturated ammonium chloride solution. The precipitate obtained is purified by chromatography on a silica column using a mixture of dichloromethane/methanol/ammonium hydroxide (98/2/0.2) as eluant to yield, after converting to a salt in ethanol in the warm state using 1N ethereal HCl, the title product.
Melting point: 260-262° C.

EXAMPLE 20

Sodium 2-[(trans-4-{2-[(3aS,9bR)-8-cyano-1,3a,4,9b-tetrahydrochromeno[3,4-c]pyrrol-2(3H)-yl]
ethyl}cyclohexyl)amino]-3,4-dioxocyclobuten-1-olate Step A: (3aS,9bR)-2-(2-{trans-4-[(2-Ethoxy-3,4-dioxocyclobuten-1-yl)amino]-cyclohexyl}ethyl)-1,2,3,3a,4,9b-hexahydrochromeno[3,4-c]pyrrole-8-carbonitrile 2 g of the compound of Example 1 (6.15 mmol) and 0.9 ml of diethyl squarate are stirred at ambient temperature for 2 hours in 15 ml of ethanol. After adding water, the crystals obtained are filtered off and dried in a desiccator to yield the title product in the form of a white powder.

Step B: Sodium 2-[(trans-4-{2-[(3aS,9bR)-8-cyano-1,3a,4,9b-tetrahydrochromeno[3,4-c]pyrrol-2(3H)-yl]ethyl}cyclohexyl)amino]-3,4-dioxocyclobuten-1-olate 1.3 g of the product obtained in the Step above are suspended in a solution of 29 ml of water and 6 ml of ethanol with 289 mg of sodium hydroxide pellets at 90° C. Acetone is added to the cooled solution, and the precipitate obtained, corresponding to the title product, is filtered off.
Mass spectrometry: [M+H]$^+$=421

EXAMPLE 21

(3aS,9bR)-2-{2-[trans-4-[(2-Amino-3,4-dioxocyclobuten-1-yl)amino]cyclohexyl]ethyl}-1,2,3,3a,4,9b-hexahydrochromeno[3,4-c]pyrrole-8-carbonitrile hydrochloride A solution of 1.17 g of the compound obtained in Step A of Example 20 (2.61 mmol) in 13 ml of ethanol is treated with 13 ml of a saturated solution of ammonia in acetonitrile for 16 hours. The solid obtained is filtered off and then washed with ethyl acetate to finally yield, after converting to a salt in ethanol in the warm state using 1N ethereal HCl, the title product.
Melting point: 325° C.
Elemental Microanalysis:

|  | C | H | N | Cl |
|---|---|---|---|---|
| theoretical % | 63.08 | 6.40 | 12.26 | 7.76 |
| experimental % | 62.60 | 6.28 | 11.95 | 7.76 |

EXAMPLE 22

(3aS,9bR)-2-{2-[trans-4-(Methylamino)cyclohexyl]ethyl}-1,2,3,3a,4,9b-hexahydrochromeno[3,4-c]pyrrole-8-carbonitrile dihydrochloride The title product is obtained according to the procedure described in Example 1 using the compound obtained in Preparation 4 as starting material.
Melting point: 320° C.
Elemental Microanalysis:

|  | C | H | N | Cl |
|---|---|---|---|---|
| theoretical % | 61.16 | 7.58 | 10.19 | 17.19 |
| experimental % | 60.96 | 7.30 | 10.09 | 17.28 |

EXAMPLE 23

N-(trans-4-{2-[(3aS,9bR)-8-cyano-1,3a,4,9b-tetrahydrochromeno[3,4-c]pyrrol-2(3H)-yl]ethyl}cyclohexyl)-N-methylacetamide hydrochloride The title product is obtained according to the procedure described in Example 2 using as starting material the compound of Example 22 instead of the compound of Example 1.
Melting point: 248° C.
Elemental Microanalysis:

|  | C | H | N | Cl |
|---|---|---|---|---|
| theoretical % | 66.09 | 7.72 | 10.05 | 8.48 |
| experimental % | 65.06 | 7.18 | 9.82 | 8.89 |

EXAMPLE 24

N-(trans-4-{2-[(3aS,9bR)-8-cyano-1,3a,4,9b-tetrahydrochromeno[3,4-c]pyrrol-2(3H)-yl]ethyl}cyclohexyl)-N-methylcyclobutanecarboxamide hydrochloride The title product is obtained according to the procedure described in Example 3 using as starting material the compound of Example 22 instead of the compound of Example 1.
Melting point: 244° C.
Elemental Microanalysis:

|  | C | H | N | Cl |
|---|---|---|---|---|
| theoretical % | 68.18 | 7.92 | 9.17 | 7.74 |
| experimental % | 67.55 | 7.23 | 9.06 | 7.69 |

EXAMPLE 25

(3aS,9bR)-2-{2-[trans-4-(Dimethylamino)cyclohexyl]ethyl}-1,2,3,3a,4,9b-hexahydrochromeno[3,4-c]pyrrole-8-carbonitrile dihydrochloride To a solution of 0.685 g of the compound of Example 1 (1.95 mmol) in 18 ml of methanol there are added, at 0° C., 0.245 g of sodium cyanoborohydride, 0.56 ml of acetic acid and then, dropwise, 0.4 ml of 37% formaldehyde solution in water. After stirring for 4 hours, 2 ml of saturated aqueous potassium carbonate solution are added. After evaporating off the solvents and then diluting with water, the mixture is extracted with ethyl acetate, dried ($MgSO_4$) and evaporated. The residue obtained is purified by chromatography on a silica column using a mixture of dichloromethane/methanol/ammonium hydroxide (80/20/2) as eluant to yield, after converting to a salt in ethanol in the warm state using 1N ethereal HCl, the title product.
Melting point: 305° C.
Elemental Microanalysis:

|  | C | H | N | Cl |
|---|---|---|---|---|
| theoretical % | 61.97 | 7.80 | 9.85 | 16.63 |
| experimental % | 61.98 | 7.52 | 9.43 | 16.42 |

EXAMPLE 26

(3aS,9bR)-2-{2-[trans-4-(Pyridin-2-ylamino)cyclohexyl]ethyl}-1,2,3,3a,4,9b-hexahydrochromeno[3,4-c]pyrrole-8-carbonitrile dihydrochloride A mixture of 0.482 g of the compound of Example 1 (1.48 mmol) and 0.245 ml of diisopropylethylamine in 5 ml of 2-fluoropyridine is heated at reflux for 24 hours. After evaporating off the solvents and then diluting with water, the mixture is extracted with ethyl acetate, dried ($MgSO_4$) and evaporated. The residue obtained is purified by chromatography on a silica column using a mixture of dichloromethane/methanol/ammonium hydroxide (97/3/0.3) as eluant to yield, after converting to a salt in ethanol in the warm state using 1N ethereal HCl, the title product.
Melting point: 305° C.
Elemental Microanalysis:

|  | C | H | N | Cl |
|---|---|---|---|---|
| theoretical % | 63.15 | 6.78 | 11.78 | 14.91 |
| experimental % | 63.11 | 6.57 | 11.09 | 14.52 |

EXAMPLE 27

(3aS,9bR)-2-[2-{trans-4-(Pyrimidin-2-ylamino)cyclohexyl]ethyl}-1,2,3,3a,4,9b-hexahydrochromeno[3,4-c]pyrrole-8-carbonitrile dihydrochloride A suspension of 0.715 g of the compound of Example 1 (2.2 mmol), 0.303 mg of 2-chloropyrimidine and 0.47 g of sodium carbonate in 45 ml of ethanol is heated at reflux for 72 hours. After filtering, the solvents are then evaporated off After extraction with ethyl acetate and drying ($MgSO_4$), evaporation yields an oil which is purified by chromatography on a silica column using a mixture of dichloromethane/methanol/ammonium hydroxide (98/2/0.2) as eluant to yield, after converting to a salt in ethanol in the warm state using 1N ethereal HCl, the title product.
Melting point: 234° C.

Elemental Microanalysis:

|  | C | H | N | Cl |
| --- | --- | --- | --- | --- |
| theoretical % | 60.50 | 6.56 | 14.70 | 14.88 |
| experimental % | 60.75 | 6.26 | 14.58 | 14.24 |

Pharmacological Study

EXAMPLE A

Determination of Affinity for Human $D_3$, $D_{2S}$ and $D_{2L}$ Receptors Stably Expressed in CHO Cells The affinity of the compounds for human $D_3$, $D_{2S}$ and $D_{2L}$ dopaminergic receptors is assessed by competition experiments using tritiated spiperone ([$^3$H]-spiperone) on CHO cell membranes stably expressing these 3 sub-types of receptor. The various cell lines are cultured to confluence and then the cells are detached and are homogenised using a Polytron in a Tris-HCl buffer (50 mM, pH 7.4) containing 5 mM $MgCl_2$. The cell debris is then centrifuged (15 minutes at 4° C.) and the sediment is taken up in an appropriate volume of HEPES buffer (20 mM) containing 150 mM NaCl and is frozen at −80° C. On the day of the experiment, the membranes are taken up in incubation buffer containing 50 mM Tris (pH 7.4), 120 mM NaCl, 5 mM KCl, 2 mM $CaCl_2$ and 5 mM $MgCl_2$. The membranes are then incubated for 1 hour at 30° C. with the compound being studied, in the presence of 0.5 nM [$^3$H]-spiperone. The non-specific binding is determined using 10 μM raclopride. At the end of the incubation period, the samples are filtered through Unifilter GF/B type filters pre-treated with PEI (0.1%) and washed several times with Tris-HCl filtration buffer (50 mM, pH 7.4) containing 120 mM NaCl. The radioactivity retained on the filters is counted after addition of scintillation liquid, with the aid of a scintillation counter. The isotherms obtained are analysed by non-linear regression to determine the $IC_{50}$ values, which are converted into $pK_a$ using the Cheng-Prusoff equation:

$$K_i = IC_{50}/(1+L/K_d)$$

wherein L represents the concentration of radioligand and $K_d$ is the dissociation constant of [$^3$H]-spiperone on the $D_3$, $D_{2S}$ and $D_{2L}$ dopaminergic receptors (0.26, 0.14 and 0.156, respectively). The results are expressed in terms of $pK_i = -\log K_i$.

|  | Affinity ($pK_i$) | | |
| --- | --- | --- | --- |
|  | $hD_3$ | $hD_{2L}$ | $hD_{2S}$ |
| Example 2 | 8.70 ± 0.05 | 7.0 ± 0.04 | 6.93 ± 0.04 |
| Example 3 | 8.73 ± 0.11 | 7.30 ± 0.05 | 7.25 ± 0.11 |

EXAMPLE B

Inhibition of Induction of Hypothermia Induced by the Dopaminergic Agonist PD128,907

In male rats of the Wistar strain, the baseline (rectal) temperature is measured and then the compound under test or the vehicle is administered by the oral route. Sixty minutes later, PD128,907 (0.63 mg/kg, s.c.), a $D_3/D_2$ dopaminergic agonist, is injected. Thirty minutes later, the body temperature is re-determined and the difference (Δ) from the baseline temperature is calculated.

| Treatment T-60 min | Dose (mg/kg, p.o.) | Treatment T0 | Dose (mg/kg, s.c.) | Δ (° C.) ± S.E.M.s | $ID_{50}$ (mg/kg, p.o.) |
| --- | --- | --- | --- | --- | --- |
| Vehicle | 0 | Vehicle | 0 | +0.36 ± 0.12 | 1.33 |
| Vehicle | 0 | PD128,907 | 0.63 | −1.63 ± 0.25 § | |
| Example 2 | 0.04 | PD128,907 | 0.63 | −1.73 ± 0.26 | |
|  | 0.16 | PD128,907 | 0.63 | −1.33 ± 0.11 | |
|  | 0.63 | PD128,907 | 0.63 | −0.97 ± 0.28 | |
|  | 2.5 | PD128,907 | 0.63 | −0.4 ± 0.13 * | |
|  | 10.0 | PD128,907 | 0.63 | +0.1 ± 0.33 * | |
| Vehicle | 0 | Vehicle | 0 | +0.68 ± 0.10 | 0.64 |
| Vehicle | 0 | PD128,907 | 0.63 | −1.60 ± 0.22 § | |
| Example 3 | 0.04 | PD128,907 | 0.63 | −1.65 ± 0.09 | |
|  | 0.16 | PD128,907 | 0.63 | −1.62 ± 0.07 | |
|  | 0.63 | PD128,907 | 0.63 | −0.83 ± 0.20 * | |
|  | 2.5 | PD128,907 | 0.63 | −0.33 ± 0.16 * | |
|  | 10.0 | PD128,907 | 0.63 | +0.35 ± 0.18 * | |

$ID_{50}$ = Inhibitory $Dose_{50}$
§ Significant difference versus "Vehicle + Vehicle" (Student's t test, P < 0.05)
* Significant difference versus "Vehicle + PD128,907" (Dunnett's test after ANOVA, P < 0.05).

In the presence of the vehicle, PD 128,907 brings about hypothermia which is blocked in dose-dependent manner by the compound of Example 3, demonstrating $D_3/D_2$ receptor antagonist activity.

EXAMPLE C

Pharmaceutical Composition

Formula for the preparation of 1000 tablets each containing 10 mg of N-(trans-4-{2-[(3aS,9bR)-8-cyano-1,3a,4,9b-tetrahydrochromeno[3,4-c]pyrrol-2(3H)-yl]ethyl}-

| | |
| --- | --- |
| cyclohexyl)cyclobutanecarboxamide hydrochloride (Example 3) | 10 g |
| Hydroxypropylcellulose | 2 g |
| Wheat starch | 10 g |
| Lactose | 100 g |
| Magnesium stearate | 3 g |
| Talc | 3 g |

The invention claimed is:
1. A compound selected from those of formula (I):

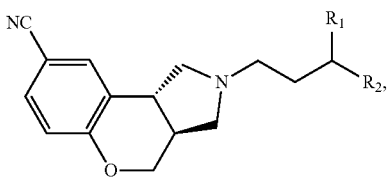

wherein $R_1$ and $R_2$ together form the following carbon-containing chain:

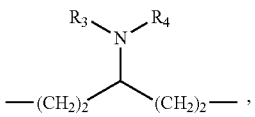

wherein:
  $R_3$ represents a hydrogen atom or a linear or branched $(C_1-C_6)$alkyl group,
  $R_4$ represents:
    a hydrogen atom,
    a linear or branched $(C_1-C_6)$alkyl, aryl, heteroaryl or 3,4-dioxocyclobutenyl group, each of those groups optionally, being substituted by one or more identical or different groups selected from halogen; linear or branched $(C_1-C_6)$alkyl; linear or branched $(C_1-C_6)$alkylcarbonyl; carboxy; hydroxy; cyano; nitro; aminocarbonyl which is unsubstituted or substituted by one or more linear or branched $(C_1-C_6)$alkyl groups; and amino which is unsubstituted or substituted by one or two linear or branched $(C_1-C_6)$alkyl groups,
    a —$COR_5$ group,
    an —$SO_2R_5$ group,
  $R_5$ represents a linear or branched $(C_1-C_6)$alkyl, $(C_3-C_8)$cycloalkyl, heterocycloalkyl, aryl or heteroaryl group, each of those groups optionally being substituted by one or more identical or different groups selected from halogen; linear or branched $(C_1-C_6)$alkyl; linear or branched $(C_1-C_6)$alkylcarbonyl; carboxy; hydroxy; cyano; nitro; aminocarbonyl which is unsubstituted or substituted by one or more linear or branched $(C_1-C_6)$alkyl groups; and amino which is unsubstituted or substituted by one or two linear or branched $(C_1-C_6)$alkyl groups,
  or $R_3$ and $R_4$, together with the nitrogen atom carrying them, form a 5- to 8-membered ring, the ring thereby defined optionally being substituted by one or more identical or different groups selected from halogen; linear or branched $(C_1-C_6)$alkyl; hydroxy; oxo; and amino which is unsubstituted or substituted by one or two linear or branched $(C_1-C_6)$alkyl groups,
its positional isomers, enantiomers, diastereoisomers, and addition salts thereof with a pharmaceutically acceptable acid or base.

2. The compound of claim 1, wherein $R_3$ represents a hydrogen atom or a methyl group.
3. The compound of claim 1, wherein $R_4$ represents a hydrogen atom or a linear or branched $(C_1-C_6)$alkyl group.
4. The compound of claim 1, wherein $R_4$ represents a —$COR_5$ group.
5. The compound of claim 1, wherein $R_4$ represents an —$SO_2R_5$ group.
6. The compound of claim 1, wherein $R_5$ represents a linear or branched $(C_1-C_6)$alkyl group.
7. The compound of claim 1, wherein $R_5$ represents an optionally substituted $(C_3-C_8)$cycloalkyl group.
8. The compound of claim 1, wherein $R_5$ represents an optionally substituted aryl group.
9. The compound of claim 1, wherein $R_5$ represents an optionally substituted heteroaryl group.
10. The compound of claim 1, wherein $R_3$ and $R_4$ together with the nitrogen atom carrying them form an optionally substituted 5-membered ring.
11. The compound of claim 1, which is selected from:
  (3aS,9bR)-2-[2-(trans-4-aminocyclohexyl)ethyl]-1,2,3,3a,4,9b-hexahydro-chromeno[3,4-c]pyrrole-8-carbonitrile;
  (3aS,9bR)-2-{2-[trans-4-(methylamino)cyclohexyl]ethyl}-1,2,3,3a,4,9b-hexahydro-chromeno[3,4-c]pyrrole-8-carbonitrile;
  (3aS,9bR)-2-{2-[trans-4-(dimethylamino)cyclohexyl]ethyl}-1,2,3,3a,4,9b-hexahydrochromeno[3,4-c]pyrrole-8-carbonitrile;
  N-(trans-4-{2-[(3aS,9bR)-8-cyano-1,3a,4,9b-tetrahydrochromeno[3,4-c]pyrrol-2(3H)-yl]ethyl}cyclohexyl)acetamide;
  N-(trans-4-{2-[(3aS,9bR)-8-cyano-1,3a,4,9b-tetrahydrochromeno[3,4-c]pyrrol-2(3H)-yl]ethyl}cyclohexyl)-2,2-dimethylpropanamide;
  N-(trans-4-{2-[(3aS,9bR)-8-cyano-1,3a,4,9b-tetrahydrochromeno[3,4-c]pyrrol-2(3H)-yl]ethyl}cyclohexyl)-N-methylacetamide;
  N-(trans-4-{2-[(3aS,9bR)-8-cyano-1,3a,4,9b-tetrahydrochromeno[3,4-c]pyrrol-2(3H)-yl]ethyl}cyclohexyl)cyclobutanecarboxamide;
  N-(trans-4-{2-[(3aS,9bR)-8-cyano-1,3a,4,9b-tetrahydrochromeno[3,4-c]pyrrol-2(3H)-yl]ethyl}cyclohexyl)cyclopropanecarboxamide;
  N-(trans-4-{2-[(3aS,9bR)-8-cyano-1,3a,4,9b-tetrahydrochromeno[3,4-c]pyrrol-2(3H)-yl]ethyl}cyclohexyl)-3,3-difluorocyclobutanecarboxamide;
  cis-N-(trans-4-{2-[(3aS,9bR)-8-cyano-1,3a,4,9b-tetrahydrochromeno[3,4-c]pyrrol-2(3H)-yl]ethyl}cyclohexyl)-3-hydroxycyclobutanecarboxamide;
  N-(trans-4-{2-[(3aS,9bR)-8-cyano-1,3a,4,9b-tetrahydrochromeno[3,4-c]pyrrol-2(3H)-yl]ethyl}cyclohexyl)-N-methylcyclobutanecarboxamide;
  N-(trans-4-{2-[(3aS,9bR)-8-cyano-1,3a,4,9b-tetrahydrochromeno[3,4-c]pyrrol-2(3H)-yl]ethyl}cyclohexyl)benzamide;
  4-chloro-N-(trans-4-{2-[(3aS,9bR)-8-cyano-1,3a,4,9b-tetrahydrochromeno[3,4-c]pyrrol-2(3H)-yl]ethyl}cyclohexyl)benzamide;
  N-(trans-4-{2-[(3aS,9bR)-8-cyano-1,3a,4,9b-tetrahydrochromeno[3,4-c]pyrrol-2(3H)-yl]ethyl}cyclohexyl)-4-fluorobenzenesulphonamide;
  4-chloro-N-(trans-4-{2-[(3aS,9bR)-8-cyano-1,3a,4,9b-tetrahydrochromeno[3,4-c]pyrrol-2(3H)-yl]ethyl}cyclohexyl)benzenesulphonamide;
  N-(trans-4-{2-[(3aS,9bR)-8-cyano-1,3a,4,9b-tetrahydrochromeno[3,4-c]pyrrol-2(3H)-yl]ethyl}cyclohexyl)-3-pyridinesulphonamide; and
  (3aS,9bR)-2-{2-[trans-4-(2-oxopyrrolidin-1-yl)cyclohexyl]ethyl}-1,2,3,3a,4,9b-hexahydrochromeno[3,4-c]pyrrole-8-carbonitrile.

12. A pharmaceutical composition comprising as active ingredient compound of claim 1, alone or in combination with one or more inert, non-toxic and pharmaceutically acceptable excipients or carriers.

13. A method of treating a condition selected from schizophrenia, paranoia, auditory and visual hallucinations, psychotic mania, abuse of drugs, anxious states, toxicomania, unipolar and bipolar depressive states, obsessive-compulsive disorders, aggressiveness, Parkinson's disease, essential tremor, dementias, autistic spectrum disorder, attention-deficit hyperactivity disorder, pain, nausea, and premature ejaculation and/or for providing renal protection, in a subject in need thereof comprising administration of an effective amount of a compound of claim 1.

* * * * *